United States Patent
Li et al.

(10) Patent No.: US 11,142,781 B2
(45) Date of Patent: Oct. 12, 2021

(54) METHOD FOR PRODUCING HIGH QUALITY MALTODEXTRIN

(71) Applicant: Jiangnan University, Wuxi (CN)

(72) Inventors: Zhaofeng Li, Wuxi (CN); Zhengbiao Gu, Wuxi (CN); Zhe Wang, Wuxi (CN); Caiming Li, Wuxi (CN); Sijia Xu, Wuxi (CN); Li Cheng, Wuxi (CN); Yan Hong, Wuxi (CN)

(73) Assignee: Jiangnan University, Wuxi (CN)

( * ) Notice: Subject to any disclaimer, the term of this patent is extended or adjusted under 35 U.S.C. 154(b) by 45 days.

(21) Appl. No.: 16/747,022

(22) Filed: Jan. 20, 2020

(65) Prior Publication Data

US 2020/0157592 A1 May 21, 2020

Related U.S. Application Data

(63) Continuation of application No. PCT/CN2018/095880, filed on Jul. 17, 2018.

(30) Foreign Application Priority Data

Jun. 29, 2018 (CN) .......................... 201810695009.7

(51) Int. Cl.
*C12P 19/18* (2006.01)
*C12P 19/04* (2006.01)

(52) U.S. Cl.
CPC .............. *C12P 19/18* (2013.01); *C12P 19/04* (2013.01)

(58) Field of Classification Search
CPC .......... C12P 19/18; C12P 19/04; C08B 30/18; C12N 9/107
USPC ........................................................ 536/103
See application file for complete search history.

(56) References Cited

U.S. PATENT DOCUMENTS 7,582,453 B2 * 9/2009 Zhong .................... C12P 19/14
435/101
2013/0323799 A1 12/2013 Takaha et al.

FOREIGN PATENT DOCUMENTS

| CN | 1444660 | A |   | 9/2003 |
| CN | 101198703 | A |   | 6/2008 |
| CN | 101613729 | A |   | 12/2009 |
| CN | 101696437 | A |   | 4/2010 |
| CN | 102392064 | A |   | 3/2012 |
| CN | 103060402 |   | * | 4/2013 |
| CN | 103404764 | A |   | 11/2013 |
| CN | 103667388 | A |   | 3/2014 |
| CN | 107653278 | A |   | 2/2018 |

OTHER PUBLICATIONS

Kittisuban et al. Slow glucose release property of enzyme-synthesized highlybranched maltodextrins differs among starch sources. Carbohydrate Polymers 107 (2014) 182-191. (Year: 2014).*

* cited by examiner

*Primary Examiner* — Yih-Horng Shiao
(74) *Attorney, Agent, or Firm* — IPro, PLLC

(57) ABSTRACT

The disclosure herein relates to a method for producing high-quality maltodextrin, and belongs to the technical field of maltodextrin. On the basis of a traditional enzymatic production process of maltodextrin, starch branching enzyme derived from *Rhodothermus obamensis* is introduced, an α-1,4-glycosidic bond is cleaved, the cleaved short chain is ligated to a receptor chain to form an α-1,6-branch point, so the degree of branching is increased and the maltodextrin has more cluster structures. Thereby, the aims that the stability of the maltodextrin is enhanced and the maltodextrin is not easy to retrograde are achieved, and the freeze-thaw stability of the maltodextrin is also improved. The method specifically comprises the steps of slurry preparation, spray liquefaction, starch branching enzyme action, filtration, decolorization, ion exchange, concentration, spray drying, and the like. The method can produce high-quality maltodextrin with good solubility and high transparency, good viscosity stability and good freeze-thaw stability during storage.

14 Claims, No Drawings

METHOD FOR PRODUCING HIGH QUALITY MALTODEXTRIN

TECHNICAL FIELD

The disclosure herein relates to a method for producing high-quality maltodextrin, and belongs to the technical field of maltodextrin.

BACKGROUND

Maltodextrin, also known as water-soluble dextrin or enzymatic dextrin, is a starch hydrolysate obtained by an acid process or enzymatic treatment. The main components of maltodextrin are dextrin, polysaccharides, oligosaccharides, and also a small amount of maltose and glucose. The DE value (reducing sugar equivalent) is usually used to indicate the degree of starch degradation, and conventional maltodextrin is a starch hydrolysate with a DE value less than 20. In recent years, maltodextrin has been widely used in the food industry. When the DE value is 2-4, maltodextrin can produce the texture and taste of fat, and can be used as a fat substitute for moon cake, salad, ice cream, sausage, and the like. When the DE value is 5-7, maltodextrin has the characteristics of low sweetness, low hygroscopicity, good film-forming property, and the like, and can be used as a thickener, a stabilizer, a filler, a carrier, and the like in foods. When the DE value is 9-12, maltodextrin is not easily damp, is difficult to brown, and can be used in food to improve the touch of the food and produce high viscosity. When the DE value is 15-20, maltodextrin has high fluidity, good solubility and suitable viscosity, and can be applied to candy, beverage, convenience food and canned food.

At present, the production of maltodextrin at home and abroad is carried out by an enzymatic process, and the acid process has been basically eliminated. However, the maltodextrin produced by the traditional enzymatic process has certain limitations. The maltodextrin has a high linear molecular content, and macromolecular polymerization will show a tendency to retrogradation during storage, thereby making a solution turbid. Since many manufacturers still cannot overcome the phenomenon of dextrin retrogradation, domestic maltodextrin products still have a big gap compared with some similar products abroad, and thus the products are greatly limited in production and application.

SUMMARY

In order to solve the above problems, the disclosure introduces a starch branching enzyme (1,4-α-glucan branching enzyme; EC 2.4.1.18) derived from *Rhodothermus obamensis* based on a traditional enzymatic production process of maltodextrin. The starch branching enzyme is able to catalyze the cleavage of α-1,4-glycosidic bonds in starch molecules, resulting in short chains with non-reducing ends. The cleaved short chain is ligated to a receptor chain in an α-1,6-glycosidic bond form by transglycosylation to form an α-1,6-branch point, thereby completing a branching process. Thereby, the stability of the maltodextrin is enhanced, the maltodextrin is not easy to retrograde, and the freeze-thaw stability of the maltodextrin is also improved. The method of the disclosure can produce high-quality maltodextrin with good solubility and high transparency, good viscosity stability and good freeze-thaw stability during storage, and improves the commodity value of the maltodextrin.

The disclosure provides a method for producing high-quality maltodextrin, sequentially comprising the following steps: slurry preparation, spray liquefaction, action of *Rhodothermus obamensis*-derived starch branching enzyme, filtration, decolorization, ion exchange and concentration.

In an embodiment of the disclosure, the method further comprises a spray drying step.

In an embodiment of the disclosure, the method is specifically as follows:

(1) slurry preparation: preparing starch milk of a certain concentration from starch, heating and insulating for a period of time, adding high temperature resistant α-amylase and calcium chloride, and adjusting pH after uniform stirring;

(2) spray liquefaction: carrying out spraying with a low pressure steam spray liquefier;

(3) starch branching enzyme action: after liquefied liquid in (2) is cooled, adding the starch branching enzyme, adjusting the pH, carrying out a reaction at a certain temperature for a period of time, and carrying out enzyme deactivation by heating to obtain reaction liquid;

(4) filtration: after the reaction liquid is cooled, carrying out filtration to obtain a settled solution;

(5) decolorization: adjusting the pH of the solution, adding activated carbon, and stirring the solution for decolorization at a certain temperature for a period of time;

(6) ion exchange: removing metal salt and pigment from the solution using ion exchange resin;

(7) concentration: concentrating the solution under a certain vacuum degree and temperature.

In an embodiment of the disclosure, the starch in the (1) is one or more of common maize starch, tapioca starch, potato starch, waxy maize starch, sweet potato starch, rice starch or wheat starch; the concentration of the starch milk is 5-45%; the starch milk is heated to 60-70° C. and thermally insulated; the high temperature resistant α-amylase is added in an amount of 10-15 U/g starch on a dry basis, and the pH is adjusted to 5.5-6.5 after the α-amylase is added; and calcium chloride is added in an amount of 0.1-0.2% on a dry basis.

In an embodiment of the disclosure, the (2) comprises 2 times of spraying; after first spraying, thermal insulation liquefying is carried out for a period of time; and then second spraying enzyme deactivation is carried out.

In an embodiment of the disclosure, during first spraying in the (2), material pressure is 0.35 MPa, steam pressure is 0.1 MPa, temperature is 102-110° C., and the time is 5-15 min; then thermal insulation liquefying is carried out at 85-95° C. for 10-90 min; and during second spraying, the material pressure is 0.35 MPa, the steam pressure is 0.3 MPa, the temperature is 130-140° C., and the time is 5 min.

In an embodiment of the disclosure, the liquefied liquid in the (3) needs to be cooled to 50° C. or lower to add the starch branching enzyme; the starch branching enzyme is derived from *Rhodothermus obamensis*; and is added in an amount of 10-500 U/g starch on a dry basis; and after the starch branching enzyme is added, the pH is adjusted to 6.0-7.5, and the reaction is carried out at 50-70° C. for 2-12 h.

In an embodiment of the disclosure, the starch branching enzyme in the (3) acts at a pH of 6.5-7.5, and the reaction is carried out at 65-70° C. for 6 h or more.

In an embodiment of the disclosure, the filtration in the (4) is carried out by a plate-and-frame filter press.

In an embodiment of the disclosure, the pH of the solution in the (5) is adjusted to 4.0-5.0, the amount of activated carbon added is 1%, and the temperature is maintained at 80-90° C. for 15-30 min for decolorization.

In an embodiment of the disclosure, the ion exchange resin used in the (6) is structurally strongly acidic cation-weakly basic anion-strongly acidic cation exchange resin, and the temperature is 40-50° C.

In an embodiment of the disclosure, the vacuum degree in the (7) is 80-90 KPa, the temperature is 40-50° C., and the solution is concentrated to a concentration of 40-50%.

In an embodiment of the disclosure, the method further comprises the step (8) of spray drying: concentrate obtained in the step (7) is spray-dried into powder, and a DE value thereof is determined.

In an embodiment of the disclosure, inlet air temperature in the (8) is 160-170° C., outlet air temperature is 75-85° C., and a feed flow rate is 18-22 mL/min.

In an embodiment of the disclosure, the starch branching enzyme is derived from *Rhodothermus obamensis* (GenBank: AB060080.1).

In an embodiment of the disclosure, the DE value of the high-quality maltodextrin produced by the method is 2-20.

The disclosure further claims the high-quality maltodextrin produced by the method.

The disclosure further claims application of the method in the fields of food, chemical industry and medicine.

Beneficial Effects of the Disclosure

In the storage process of maltodextrin produced by the traditional enzymatic method, a retrogradation phenomenon appears due to linear macromolecular polymerization, which affects the application of maltodextrin products. In the disclosure, on the basis of an enzymatic production process of maltodextrin, the starch branching enzyme derived from *Rhodothermus obamensis* is introduced to improve the branching degree, and the produced maltodextrin has good solubility and high transparency, good viscosity stability and improved freeze-thaw stability during storage. For the maltodextrin of DE 10, the maltodextrin obtained by the disclosure dissolves faster than maltodextrin produced by the conventional method, the transparency can be increased from 0.2% to 97.6% when stored for 60 d, and the viscosity during storage is very stable, which can meet the market demand. In addition, for the maltodextrin of DE 5, the method of the disclosure can increase the transparency from 1.7% to 38.2% after 5 freeze-thaw cycles without changing the DE value. For the maltodextrin of DE 10, the method of the disclosure can increase the transparency from 4.1% to 96.8% after 5 freeze-thaw cycles without changing the DE value. For the maltodextrin of DE 15, the method of the disclosure can increase the transparency from 52.1% to 97.7% after 5 freeze-thaw cycles without changing the DE value.

The disclosure has the following four advantages compared with the effect of treatment with the starch branching enzyme derived from *G. thermoglucosidans*: (1) the disclosure broadens the range of DE values of the modifiable maltodextrin, and the starch branching enzyme derived from *Rhodothermus obamensis* and acting on the maltodextrin with a DE value of 2-20 can significantly improve the dissolution rate, and transparency and viscosity stability during storage, of the maltodextrin; (2) the maltodextrin obtained by the disclosure has obvious effects when stored at room temperature and in a refrigerated (4° C.) state; (3) the maltodextrin obtained by the disclosure can maintain improved transparency for a long time, the transparencies of the maltodextrin with DE values of 5, 10 and 15 are 99.8%, 99.8% and 99.9% respectively when stored at 4° C. for 10 d, and after storage for 60 d, the transparency can still reach 53.7%, 97.6% and 98.7%, which is obviously better than the modification effect of the starch branching enzyme derived from *G. thermoglucosidans*; and (4) the maltodextrin obtained by the disclosure not only has improved transparency and viscosity stability, but also has a faster dissolution rate.

DETAILED DESCRIPTION

Example 1: Effect of Additive Amount of Starch Branching Enzyme on Properties of Maltodextrin (1) Slurry preparation: Starch milk of 35% was prepared from starch, and was thermally insulated at 70° C. for 30 min, high temperature resistant α-amylase in an amount of 12 U/g starch on a dry basis and 0.2% calcium chloride were added, and the pH was adjusted to 6.5 after uniform stirring.

(2) Spray liquefaction: Spraying was carried out with a low pressure steam spray liquefier, where first spraying was carried out at a material pressure of 0.35 MPa, a steam pressure of 0.1 MPa and a temperature of 105° C. for 8 min; then thermal insulation liquefying was carried out at 90° C. for 40 min; and second spraying enzyme deactivation was carried out at a material pressure of 0.35 MPa, a steam pressure of 0.3 MPa and a temperature of 140° C. for 5 min.

(3) Starch branching enzyme action: After liquefied liquid in (2) was cooled to 50° C. or lower, starch branching enzyme derived from *Rhodothermus obamensis* was added in an amount of 100, 200, 300, 400 and 500 U/g on a dry basis respectively, the pH was adjusted to 7.0, a reaction was carried out at 65° C. for 6 h, and reaction liquid was obtained after enzyme deactivation by heating.

(4) Filtration: After the reaction liquid was cooled, filtration was carried out by a plate-and-frame filter press to obtain a settled solution.

(5) Decolorization: The pH of the solution was adjusted to 4.5, 1% activated carbon was added, and the solution was stirred for decolorization at 85° C. for 40 min.

(6) Ion exchange: Metal salt and pigment were removed from the solution at 45° C. using strongly acidic cation-weakly basic anion-strongly acidic cation exchange resin.

(7) Concentration: The solution was concentrated to a concentration of 50% at a vacuum degree of 85 KPa and a temperature of 45° C.

(8) Spray drying: The concentrated liquid obtained in (7) was spray-dried into powder at an inlet air temperature of 170° C., an outlet air temperature of 85° C., and a feed flow rate of 18 mL/min, and the DE value of the powder was measured.

The effect of the additive amount of the starch branching enzyme on the properties of maltodextrin is shown in Tables 1 and 2. After the starch branching enzyme derived from *Rhodothermus obamensis* was introduced, the solubility, transparency and viscosity stability of the maltodextrin were all significantly improved without changing the DE value of the maltodextrin, and high-quality maltodextrin was obtained. When the additive amount of the starch branching enzyme was increased to 200 U/g or more, the difference in the properties of maltodextrin was small and the production cost was increased. When the starch branching enzyme derived from *G. thermoglucosidans* was introduced, almost no effect was found.

Control A represents the maltodextrin produced in case of lacking step (3).

Control B represents the maltodextrin produced by the starch branching enzyme derived from *G. thermoglucosidans* substituted for the *Rhodothermus obamensis*-derived starch branching enzyme in step (3) in an amount of 200 U/g.

Control C represents the maltodextrin prepared by the starch branching enzyme derived from *G. thermoglucosidans* substituted for the *Rhodothermus obamensis*-derived starch branching enzyme in step (3) by reaction under the optimum reaction conditions of *G. thermoglucosidans*. The optimum reaction conditions were specifically as follows: the amount of the starch branching enzyme added was 0.12 U/g, the reaction temperature was 45° C., the reaction time was 4 h, and the pH of the reaction was adjusted to 6.5.

TABLE 1

Effect of additive amount of starch branching enzyme on properties of maltodextrin

| Additive amount (U/g) | DE value | Solubility[1] | Transparency[2] |
|---|---|---|---|
| Control A | 10.1 | 3 min 25 s | 0.2% |
| 100 | 10.0 | 3 min 14 s | 57.4% |
| 200 | 9.9 | 2 min 23 s | 97.6% |
| 300 | 10.3 | 2 min 19 s | 97.9% |
| 400 | 10.2 | 2 min 14 s | 98.0% |
| 500 | 10.2 | 2 min 08 s | 98.0% |
| Control B-200 | 10.3 | 3 min 25 s | 0.5% |
| Control C | 10.1 | 3 min 24 s | 0.7% |

Note:
[1]Solubility: 5 g of sample was weighed and dissolved in 50 mL of distilled water, and the time when maltodextrin was completely dissolved was taken as an indicator.
[2]Transparency: The transparency of a 30% aqueous solution of maltodextrin prepared and stored in a refrigerated (4° C.) state for 60 d.

TABLE 2

Effect of additive amount of starch branching enzyme on viscosity stability of maltodextrin

| Additive amount (U/g) | Viscosity[1] (mPa·s) | | | | | |
|---|---|---|---|---|---|---|
| | 0 d | 2 d | 4 d | 6 d | 8 d | 10 d |
| Control A | 97 | 104 | 129 | 153 | 187 | 219 |
| 100 | 94 | 98 | 103 | 114 | 121 | 132 |
| 200 | 93 | 93 | 94 | 95 | 97 | 97 |
| 300 | 91 | 92 | 91 | 93 | 93 | 94 |
| 400 | 93 | 93 | 94 | 94 | 94 | 93 |
| 500 | 92 | 92 | 92 | 92 | 93 | 93 |
| Control B-200 | 98 | 102 | 128 | 151 | 189 | 213 |
| Control C | 96 | 102 | 127 | 149 | 182 | 209 |

Note:
[1]Viscosity: The viscosity of a 50% aqueous solution of maltodextrin prepared and placed for 0, 2, 4, 6, 8 and 10 d respectively.

TABLE 3

Effect of additive amount of starch branching enzyme on freeze-thaw stability of maltodextrin

| Additive amount (U/g) | DE value | FTC1[1] | FTC3[1] | FTC5[1] |
|---|---|---|---|---|
| Control A | 10.1 | 92.0% | 43.7% | 4.1% |
| 100 | 10.0 | 94.6% | 68.1% | 37.3% |
| 200 | 9.9 | 98.6% | 97.7% | 96.8% |
| 300 | 10.3 | 98.8% | 97.9% | 96.9% |
| 400 | 10.2 | 99.4% | 98.7% | 97.5% |
| 500 | 10.2 | 99.4% | 98.6% | 97.6% |
| Control B-200 | 10.3 | 92.3% | 44.5% | 4.8% |
| Control C | 10.1 | 92.6% | 45.0% | 5.2% |

Note:
[1]FTC (freeze-thaw cycle): indicating the freeze-thaw stability of maltodextrin. FTC1, 3, and 5 respectively indicate the transparency of 30% maltodextrin after 1, 3, and 5 freeze-thaw cycles.

Transparency was represented by transmittance measured at 620 nm using a spectrophotometer.

Example 2: Effect of Action Time of Starch Branching Enzyme on Properties of Maltodextrin (1) Slurry preparation: Starch milk of 35% was prepared from starch, and was thermally insulated at 70° C. for 30 min, high temperature resistant α-amylase in an amount of 12 U/g starch on a dry basis and 0.2% calcium chloride were added, and the pH was adjusted to 6.5 after uniform stirring.

(2) Spray liquefaction: Spraying was carried out with a low pressure steam spray liquefier, where first spraying was carried out at a material pressure of 0.35 MPa, a steam pressure of 0.1 MPa and a temperature of 105° C. for 8 min; then thermal insulation liquefying was carried out at 90° C. for 40 min; and second spraying enzyme deactivation was carried out at a material pressure of 0.35 MPa, a steam pressure of 0.3 MPa and a temperature of 140° C. for 5 min.

(3) Starch branching enzyme action: After liquefied liquid in (2) was cooled to 50° C. or lower, the starch branching enzyme derived from *Rhodothermus obamensis* was added in an amount of 200 U/g on a dry basis, the pH was adjusted to 7.0, a reaction was carried out at 65° C. for 2, 4, 6, 8, 10 and 12 h respectively, and reaction liquid was obtained after enzyme deactivation by heating.

(4) Filtration: After the reaction liquid was cooled, filtration was carried out by a plate-and-frame filter press to obtain a settled solution.

(5) Decolorization: The pH of the solution was adjusted to 4.5, 1% activated carbon was added, and the solution was stirred for decolorization at 85° C. for 40 min.

(6) Ion exchange: Metal salt and pigment were removed from the solution at 45° C. using strongly acidic cation-weakly basic anion-strongly acidic cation exchange resin.

(7) Concentration: The solution was concentrated to a concentration of 50% at a vacuum degree of 85 KPa and a temperature of 45° C.

(8) Spray drying: The concentrated liquid obtained in (7) was spray-dried into powder at an inlet air temperature of 170° C., an outlet air temperature of 85° C., and a feed flow rate of 18 mL/min, and the DE value of the powder was measured.

The effect of the action time of the starch branching enzyme on the properties of maltodextrin is shown in Tables 3 and 4. After the starch branching enzyme derived from *Rhodothermus obamensis* was introduced, the solubility, transparency and viscosity stability of the maltodextrin were all significantly improved without changing the DE value of the maltodextrin, and high-quality maltodextrin was obtained. When the action time of the starch branching enzyme was increased to 6 h or more, the difference in the properties of maltodextrin was small and the production cost was increased. When the starch branching enzyme derived from *G. thermoglucosidans* was introduced, almost no effect was found.

Control A represents the maltodextrin produced in case of lacking step (3).

Control B represents the maltodextrin produced by the starch branching enzyme derived from *G. thermoglucosidans* substituted for the *Rhodothermus obamensis*-derived starch branching enzyme in step (3), and the action time was 6 h.

Control C represents the maltodextrin prepared by the starch branching enzyme derived from *G. thermoglucosidans* substituted for the *Rhodothermus obamensis*-derived starch branching enzyme in step (3) by reaction under the optimum reaction conditions of *G. thermoglucosidans*. The optimum reaction conditions were specifically as follows: the amount of the starch branching enzyme added was 0.12

U/g, the reaction temperature was 45° C., the reaction time was 4 h, and the pH of the reaction was adjusted to 6.5.

TABLE 4

Effect of action time of starch branching enzyme on properties of maltodextrin

| Action time (h) | DE value | Solubility[1] | Transparency[2] |
|---|---|---|---|
| Control A | 10.1 | 3 min 25 s | 0.2% |
| 2 | 9.9 | 3 min 09 s | 37.1% |
| 4 | 10.0 | 2 min 58 s | 66.0% |
| 6 | 9.9 | 2 min 23 s | 97.6% |
| 8 | 10.1 | 2 min 18 s | 98.3% |
| 10 | 10.3 | 2 min 15 s | 98.0% |
| 12 | 10.2 | 2 min 07 s | 98.7% |
| Control B-6 | 10.3 | 3 min 25 s | 0.5% |
| Control C | 10.1 | 3 min 24 s | 0.7% |

Note:
[1]Solubility: 5 g of sample was weighed and dissolved in 50 mL of distilled water, and the time when maltodextrin was completely dissolved was taken as an indicator.
[2]Transparency: The transparency of a 30% aqueous solution of maltodextrin prepared and stored in a refrigerated (4° C.) state for 60 d.

TABLE 5

Effect of action temperature of starch branching enzyme on viscosity stability of maltodextrin

| Action time (h) | Viscosity[1] (mPa·s) | | | | | |
|---|---|---|---|---|---|---|
| | 0 d | 2 d | 4 d | 6 d | 8 d | 10 d |
| Control A | 97 | 104 | 129 | 153 | 187 | 219 |
| 2 | 99 | 106 | 125 | 141 | 169 | 188 |
| 4 | 96 | 102 | 114 | 127 | 144 | 159 |
| 6 | 93 | 93 | 94 | 95 | 97 | 97 |
| 8 | 93 | 94 | 96 | 95 | 96 | 95 |
| 10 | 94 | 93 | 93 | 95 | 94 | 95 |
| 12 | 92 | 92 | 93 | 93 | 94 | 94 |
| Control B-6 | 98 | 102 | 128 | 151 | 189 | 213 |
| Control C | 96 | 102 | 127 | 149 | 182 | 209 |

Note:
[1]Viscosity: The viscosity of a 50% aqueous solution of maltodextrin prepared and placed for 0, 2, 4, 6, 8 and 10 d respectively.

TABLE 6

Effect of action time of starch branching enzyme on freeze-thaw stability of maltodextrin

| Action time (h) | DE value | FTC1[1] | FTC3[1] | FTC5[1] |
|---|---|---|---|---|
| Control | 10.1 | 92.0% | 43.7% | 4.1% |
| 2 | 9.9 | 94.5% | 56.7% | 21.3% |
| 4 | 10.0 | 94.6% | 70.1% | 39.9% |
| 6 | 9.9 | 98.6% | 97.7% | 96.8% |
| 8 | 10.1 | 99.0% | 98.2% | 97.7% |
| 10 | 10.3 | 99.5% | 98.9% | 98.0% |
| 12 | 10.2 | 99.3% | 98.7% | 97.9% |
| Control B-6 | 10.3 | 92.3% | 44.5% | 4.8% |
| Control C | 10.1 | 92.6% | 45.0% | 5.2% |

Note:
[1]FTC (freeze-thaw cycle): indicating the freeze-thaw stability of maltodextrin. FTC1, 3, and 5 respectively indicate the transparency of 30% maltodextrin after 1, 3, and 5 freeze-thaw cycles.

Transparency was represented by transmittance measured at 620 nm using a spectrophotometer.

Example 3: Effect of Action Temperature of Starch Branching Enzyme on Properties of Maltodextrin (1) Slurry preparation: Starch milk of 35% was prepared from starch, and was thermally insulated at 70° C. for 30 min, high temperature resistant α-amylase in an amount of 12 U/g starch on a dry basis and 0.2% calcium chloride were added, and the pH was adjusted to 6.5 after uniform stirring.

(2) Spray liquefaction: Spraying was carried out with a low pressure steam spray liquefier, where first spraying was carried out at a material pressure of 0.35 MPa, a steam pressure of 0.1 MPa and a temperature of 105° C. for 8 min; then thermal insulation liquefying was carried out at 90° C. for 40 min; and second spraying enzyme deactivation was carried out at a material pressure of 0.35 MPa, a steam pressure of 0.3 MPa and a temperature of 140° C. for 5 min.

(3) Starch branching enzyme action: After liquefied liquid in (2) was cooled to 50° C. or lower, the starch branching enzyme derived from *Rhodothermus obamensis* was added in an amount of 200 U/g, the pH was adjusted to 7.0, a reaction was carried out at 50, 55, 60, 65 and 70° C. respectively for 6 h, and reaction liquid was obtained after enzyme deactivation by heating.

(4) Filtration: After the reaction liquid was cooled, filtration was carried out by a plate-and-frame filter press to obtain a settled solution.

(5) Decolorization: The pH of the solution was adjusted to 4.5, 1% activated carbon was added, and the solution was stirred for decolorization at 85° C. for 40 min.

(6) Ion exchange: Metal salt and pigment were removed from the solution at 45° C. using strongly acidic cation-weakly basic anion-strongly acidic cation exchange resin.

(7) Concentration: The solution was concentrated to a concentration of 50% at a vacuum degree of 85 KPa and a temperature of 45° C.

(8) Spray drying: The concentrated liquid obtained in (7) was spray-dried into powder at an inlet air temperature of 170° C., an outlet air temperature of 85° C., and a feed flow rate of 18 mL/min, and the DE value of the powder was measured.

The effect of the action temperature of the starch branching enzyme on the properties of maltodextrin is shown in Tables 5 and 6. After the starch branching enzyme derived from *Rhodothermus obamensis* was introduced, the solubility, transparency and viscosity stability of the maltodextrin were all significantly improved without changing the DE value of the maltodextrin, and high-quality maltodextrin was obtained. When the action temperature of the starch branching enzyme was 65° C., the maltodextrin has the best properties. When the starch branching enzyme derived from *G. thermoglucosidans* was introduced, almost no effect was found.

Control A represents the maltodextrin produced in case of lacking step (3).

Control B represents the maltodextrin produced by the starch branching enzyme derived from *G. thermoglucosidans* substituted for the *Rhodothermus obamensis*-derived starch branching enzyme in step (3), and the action temperature was 65° C.

Control C represents the maltodextrin prepared by the starch branching enzyme derived from *G. thermoglucosidans* substituted for the *Rhodothermus obamensis*-derived starch branching enzyme in step (3) by reaction under the optimum reaction conditions of *G. thermoglucosidans*. The optimum reaction conditions were specifically as follows: the amount of the starch branching enzyme added was 0.12 U/g, the reaction temperature was 45° C., the reaction time was 4 h, and the pH of the reaction was adjusted to 6.5.

TABLE 7

Effect of action temperature of starch branching enzyme on properties of maltodextrin

| Action temperature (° C.) | DE value | Solubility[1] | Transparency[2] |
|---|---|---|---|
| Control A | 10.1 | 3 min 25 s | 0.2% |
| 50 | 10.2 | 3 min 22 s | 1.7% |
| 55 | 10.3 | 3 min 13 s | 21.6% |
| 60 | 10.2 | 2 min 58 s | 85.9% |
| 65 | 9.9 | 2 min 23 s | 97.6% |
| 70 | 10.0 | 2 min 47 s | 94.3% |
| Control B-65 | 10.3 | 3 min 25 s | 0.5% |
| Control C | 10.1 | 3 min 24 s | 0.7% |

Note:
[1]Solubility: 5 g of sample was weighed and dissolved in 50 mL of distilled water, and the time when maltodextrin was completely dissolved was taken as an indicator.
[2]Transparency: The transparency of a 30% aqueous solution of maltodextrin prepared and stored in a refrigerated (4° C.) state for 60 d.

TABLE 8

Effect of action temperature of starch branching enzyme on viscosity stability of maltodextrin

| Action temperature (° C.) | Viscosity[1] (mPa · s) | | | | | |
|---|---|---|---|---|---|---|
| | 0 d | 2 d | 4 d | 6 d | 8 d | 10 d |
| Control A | 97 | 104 | 129 | 153 | 187 | 219 |
| 50 | 98 | 103 | 130 | 149 | 181 | 203 |
| 55 | 99 | 100 | 123 | 136 | 169 | 182 |
| 60 | 97 | 99 | 104 | 117 | 131 | 148 |
| 65 | 93 | 93 | 94 | 95 | 97 | 97 |
| 70 | 94 | 98 | 104 | 112 | 117 | 124 |
| Control B-65 | 98 | 102 | 128 | 151 | 189 | 213 |
| Control C | 96 | 102 | 127 | 149 | 182 | 209 |

Note:
[1]Viscosity: The viscosity of a 50% aqueous solution of maltodextrin prepared and placed for 0, 2, 4, 6, 8 and 10 d respectively.

TABLE 9

Effect of action temperature of starch branching enzyme on freeze-thaw stability of maltodextrin

| Action temperature (° C.) | DE value | FTC1[1] | FTC3[1] | FTC5[1] |
|---|---|---|---|---|
| Control | 10.1 | 92.0% | 43.7% | 4.1% |
| 50 | 10.2 | 92.1% | 47.5% | 10.2% |
| 55 | 10.3 | 93.0% | 55.0% | 32.3% |
| 60 | 10.2 | 95.8% | 78.1% | 59.2% |
| 65 | 9.9 | 98.6% | 97.7% | 96.8% |
| 70 | 10.0 | 97.1% | 89.2% | 79.9% |
| Control B-65 | 10.3 | 92.3% | 44.5% | 4.8% |
| Control C | 10.1 | 92.6% | 45.0% | 5.2% |

Note:
[1]FTC (freeze-thaw cycle): indicating the freeze-thaw stability of maltodextrin. FTC1, 3, and 5 respectively indicate the transparency of 30% maltodextrin after 1, 3, and 5 freeze-thaw cycles.

Transparency was represented by transmittance measured at 620 nm using a spectrophotometer.

Example 4: Effect of Action pH of Starch Branching Enzyme on Properties of Maltodextrin (1) Slurry preparation: Starch milk of 35% was prepared from starch, and was thermally insulated at 70° C. for 30 min, high temperature resistant α-amylase in an amount of 12 U/g starch on a dry basis and 0.2% calcium chloride were added, and the pH was adjusted to 6.5 after uniform stirring.

(2) Spray liquefaction: Spraying was carried out with a low pressure steam spray liquefier, where first spraying was carried out at a material pressure of 0.35 MPa, a steam pressure of 0.1 MPa and a temperature of 105° C. for 8 min; then thermal insulation liquefying was carried out at 90° C. for 40 min; and second spraying enzyme deactivation was carried out at a material pressure of 0.35 MPa, a steam pressure of 0.3 MPa and a temperature of 140° C. for 5 min.

(3) Starch branching enzyme action: After liquefied liquid in (2) was cooled to 50° C. or lower, the starch branching enzyme derived from *Rhodothermus obamensis* was added in an amount of 200 U/g, the pH was adjusted to 6.0, 6.5, 7.0 and 7.5 respectively, a reaction was carried out at 65° C. for 6 h, and reaction liquid was obtained after enzyme deactivation by heating.

(4) Filtration: After the reaction liquid was cooled, filtration was carried out by a plate-and-frame filter press to obtain a settled solution.

(5) Decolorization: The pH of the solution was adjusted to 4.5, 1% activated carbon was added, and the solution was stirred for decolorization at 85° C. for 40 min.

(6) Ion exchange: Metal salt and pigment were removed from the solution at 45° C. using strongly acidic cation-weakly basic anion-strongly acidic cation exchange resin.

(7) Concentration: The solution was concentrated to a concentration of 50% at a vacuum degree of 85 KPa and a temperature of 45° C.

(8) Spray drying: The concentrated liquid obtained in (7) was spray-dried into powder at an inlet air temperature of 170° C., an outlet air temperature of 85° C., and a feed flow rate of 18 mL/min, and the DE value of the powder was measured.

The effect of the action pH of the starch branching enzyme on the properties of maltodextrin is shown in Tables 7 and 8. After the starch branching enzyme derived from *Rhodothermus obamensis* was introduced, the solubility, transparency and viscosity stability of the maltodextrin were all significantly improved without changing the DE value of the maltodextrin, and high-quality maltodextrin was obtained. When the action pH of the starch branching enzyme was 7.0, the maltodextrin has the best properties. When the starch branching enzyme derived from *G. thermoglucosidans* was introduced, almost no effect was found.

Control A represents the maltodextrin produced in case of lacking step (3).

Control B represents the maltodextrin produced by the starch branching enzyme derived from *G. thermoglucosidans* substituted for the *Rhodothermus obamensis*-derived starch branching enzyme in step (3), and the action pH was 7.0.

Control C represents the maltodextrin prepared by the starch branching enzyme derived from *G. thermoglucosidans* substituted for the *Rhodothermus obamensis*-derived starch branching enzyme in step (3) by reaction under the optimum reaction conditions of *G. thermoglucosidans*. The optimum reaction conditions were specifically as follows: the amount of the starch branching enzyme added was 0.12 U/g, the reaction temperature was 45° C., the reaction time was 4 h, and the pH of the reaction was adjusted to 6.5.

TABLE 10

Effect of action pH of starch branching enzyme on properties of maltodextrin

| Action pH | DE value | Solubility[1] | Transparency[2] |
|---|---|---|---|
| Control A | 10.1 | 3 min 25 s | 0.2% |
| 6.0 | 10.2 | 3 min 11 s | 28.5% |

TABLE 10-continued

Effect of action pH of starch branching enzyme on properties of maltodextrin

| Action pH | DE value | Solubility[1] | Transparency[2] |
|---|---|---|---|
| 6.5 | 10.0 | 2 min 37 s | 90.2% |
| 7.0 | 9.9 | 2 min 23 s | 97.6% |
| 7.5 | 10.1 | 2 min 58 s | 78.0% |
| Control B-7.0 | 10.3 | 3 min 25 s | 0.5% |
| Control C | 10.1 | 3 min 24 s | 0.7% |

Note:
[1] Solubility: 5 g of sample was weighed and dissolved in 50 mL of distilled water, and the time when maltodextrin was completely dissolved was taken as an indicator.
[2] Transparency: The transparency of a 30% aqueous solution of maltodextrin prepared and stored in a refrigerated (4° C.) state for 60 d.

TABLE 11

Effect of action pH of starch branching enzyme on viscosity stability of maltodextrin

| Action pH | Viscosity[1] (mPa · s) | | | | | |
|---|---|---|---|---|---|---|
| | 0 d | 2 d | 4 d | 6 d | 8 d | 10 d |
| Control A | 97 | 104 | 129 | 153 | 187 | 219 |
| 6.0 | 98 | 103 | 121 | 142 | 160 | 185 |
| 6.5 | 94 | 103 | 105 | 114 | 121 | 133 |
| 7.0 | 93 | 93 | 94 | 95 | 97 | 97 |
| 7.5 | 96 | 105 | 113 | 127 | 140 | 156 |
| Control B-7.0 | 98 | 102 | 128 | 151 | 189 | 213 |
| Control C | 96 | 102 | 127 | 149 | 182 | 209 |

Note:
[1] Viscosity: The viscosity of a 50% aqueous solution of maltodextrin prepared and placed for 0, 2, 4, 6, 8 and 10 d respectively.

TABLE 12

Effect of action pH of starch branching enzyme on freeze-thaw stability of maltodextrin

| Action pH | DE value | FTC1[1] | FTC3[1] | FTC5[1] |
|---|---|---|---|---|
| Control | 10.1 | 92.0% | 43.7% | 4.1% |
| 6.0 | 10.2 | 92.9% | 52.5% | 29.3% |
| 6.5 | 10.0 | 96.7% | 87.4% | 72.9% |
| 7.0 | 9.9 | 98.6% | 97.7% | 96.8% |
| 7.5 | 10.1 | 94.1% | 78.4% | 61.1% |
| Control B-7.0 | 10.3 | 92.3% | 44.5% | 4.8% |
| Control C | 10.1 | 92.6% | 45.0% | 5.2% |

Note:
[1] FTC (freeze-thaw cycle): indicating the freeze-thaw stability of maltodextrin. FTC1, 3, and 5 respectively indicate the transparency of 30% maltodextrin after 1, 3, and 5 freeze-thaw cycles.

Transparency was represented by transmittance measured at 620 nm using a spectrophotometer.

Example 5: Effect of Starch Branching Enzyme on Properties of Maltodextrin with Different DE Values (1) Slurry preparation: Starch milk of 35% was prepared from starch, and was thermally insulated at 70° C. for 30 min, high temperature resistant α-amylase in an amount of 12 U/g starch on a dry basis and 0.2% calcium chloride were added, and the pH was adjusted to 6.5 after uniform stirring.

(2) Spray liquefaction: Spraying was carried out with a low pressure steam spray liquefier, where first spraying was carried out at a material pressure of 0.35 MPa, a steam pressure of 0.1 MPa and a temperature of 105° C. for 8 min; then thermal insulation liquefying was carried out at 90° C. for 15, 40 and 60 min respectively; and second spraying enzyme deactivation was carried out at a material pressure of 0.35 MPa, a steam pressure of 0.3 MPa and a temperature of 140° C. for 5 min.

(3) Starch branching enzyme action: After liquefied liquid in (2) was cooled to 50° C. or lower, the starch branching enzyme derived from *Rhodothermus obamensis* was added in an amount of 200 U/g, the pH was adjusted to 7.0, a reaction was carried out at 65° C. for 6 h, and reaction liquid was obtained after enzyme deactivation by heating.

(4) Filtration: After the reaction liquid was cooled, filtration was carried out by a plate-and-frame filter press to obtain a settled solution.

(5) Decolorization: The pH of the solution was adjusted to 4.5, 1% activated carbon was added, and the solution was stirred for decolorization at 85° C. for 40 min.

(6) Ion exchange: Metal salt and pigment were removed from the solution at 45° C. using strongly acidic cation-weakly basic anion-strongly acidic cation exchange resin.

(7) Concentration: The solution was concentrated to a concentration of 50% at a vacuum degree of 85 KPa and a temperature of 45° C.

(8) Spray drying: The concentrated liquid obtained in (7) was spray-dried into powder at an inlet air temperature of 170° C., an outlet air temperature of 85° C., and a feed flow rate of 18 mL/min, and the DE value of the powder was measured.

The effect of the starch branching enzyme on the properties of maltodextrin with different DE values is shown in Tables 9 and 10. For maltodextrin with any DE value, the introduction of the *Rhodothermus obamensis*-derived starch branching enzyme may significantly enhance the solubility, transparency and viscosity stability to obtain high-quality maltodextrin. When the starch branching enzyme derived from *G. thermoglucosidans* was introduced, almost no effect was found.

Control A represents the maltodextrin produced in case of lacking step (3).

Control B represents the maltodextrin produced by the starch branching enzyme derived from *G. thermoglucosidans* substituted for the *Rhodothermus obamensis*-derived starch branching enzyme in step (3).

Control C represents the maltodextrin prepared by the starch branching enzyme derived from *G. thermoglucosidans* substituted for the *Rhodothermus obamensis*-derived starch branching enzyme in step (3) by reaction under optimum reaction conditions of *G. thermoglucosidans*. The optimum reaction conditions were specifically as follows: the amount of the starch branching enzyme added was 0.12 U/g, the reaction temperature was 45° C., the reaction time was 4 h, and the pH of the reaction was adjusted to 6.5.

Controls 1, 2 and 3 respectively represent maltodextrin with DE values of 5, 10 and 15 produced in step (2) for the thermal insulation liquefying time of 15, 40 and 60 min.

TABLE 13

Effect of starch branching enzyme on properties of maltodextrin with different DE values

| Thermal insulation liquefying time (min) | DE value | Solubility[1] | Transparency[2] |
|---|---|---|---|
| Control A1 | 5.2 | 8 min 47 s | 0.1% |
| 15 | 5.0 | 5 min 25 s | 53.7% |

TABLE 13-continued

Effect of starch branching enzyme on properties
of maltodextrin with different DE values

| Thermal insulation liquefying time (min) | DE value | Solubility[1] | Transparency[2] |
|---|---|---|---|
| Control B1 | 5.1 | 8 min 44 s | 0.3% |
| Control C1 | 5.2 | 8 min 42 s | 0.4% |
| Control A2 | 10.1 | 3 min 25 s | 0.2% |
| 40 | 9.9 | 2 min 23 s | 97.6% |
| Control B2 | 10.3 | 3 min 25 s | 0.5% |
| Control C2 | 10.1 | 3 min 24 s | 0.7% |
| Control A3 | 15.0 | 2 min 37 s | 24.5% |
| 60 | 15.2 | 1 min 28 s | 98.7% |
| Control B3 | 15.1 | 2 min 35 s | 24.9% |
| Control C3 | 14.9 | 2 min 33 s | 25.3% |

Note:
[1]Solubility: 5 g of sample was weighed and dissolved in 50 mL of distilled water, and the time when maltodextrin was completely dissolved was taken as an indicator.
[2]Transparency: The transparency of a 30% aqueous solution of maltodextrin prepared and stored in a refrigerated (4° C.) state for 60 d.

TABLE 14

Effect of starch branching enzyme on viscosity stability
of maltodextrin with different DE values

| Thermal insulation liquefying time (min) | Viscosity[1] (mPa · s) | | | | | |
|---|---|---|---|---|---|---|
| | 0 d | 2 d | 4 d | 6 d | 8 d | 10 d |
| Control A1 | 148 | 179 | 222 | 251 | 307 | 379 |
| 15 | 142 | 151 | 165 | 189 | 197 | 203 |
| Control B1 | 149 | 177 | 219 | 250 | 305 | 376 |
| Control C1 | 147 | 176 | 218 | 248 | 303 | 375 |
| Control 2 | 97 | 104 | 129 | 153 | 187 | 219 |
| 40 | 93 | 93 | 94 | 95 | 97 | 97 |
| Control B2 | 98 | 102 | 128 | 151 | 189 | 213 |
| Control C2 | 96 | 102 | 127 | 149 | 182 | 209 |
| Control 3 | 79 | 93 | 118 | 139 | 155 | 179 |
| 60 | 78 | 79 | 80 | 79 | 79 | 80 |
| Control B3 | 80 | 92 | 117 | 139 | 156 | 178 |
| Control C3 | 79 | 91 | 115 | 137 | 154 | 176 |

Note:
[1]Viscosity: The viscosity of a 50% aqueous solution of maltodextrin prepared and placed for 0, 2, 4, 6, 8 and 10 d respectively.

TABLE 15

Effect of starch branching enzyme on freeze-thaw stability
of maltodextrin with different DE values

| Thermal insulation liquefying time (min) | DE value | FTC1[1] | FTC3[1] | FTC5[1] |
|---|---|---|---|---|
| Control A1 | 5.2 | 78.2% | 10.3% | 1.7% |
| 15 | 5.0 | 91.2% | 69.6% | 38.2% |
| Control B1 | 5.1 | 78.9% | 10.8% | 1.9% |
| Control C1 | 5.2 | 79.2% | 11.0% | 2.2% |
| Control A2 | 10.1 | 92.0% | 43.7% | 4.1% |
| 40 | 9.9 | 98.6% | 97.7% | 96.8% |
| Control B2 | 10.3 | 92.3% | 44.5% | 4.8% |
| Control C2 | 10.1 | 92.6% | 45.0% | 5.2% |
| Control A3 | 15.0 | 93.8% | 77.2% | 52.1% |
| 60 | 15.2 | 99.5% | 98.3% | 97.7% |
| Control B3 | 15.1 | 94.0% | 77.5% | 52.8% |
| Control C3 | 14.9 | 93.9% | 78.2% | 53.1% |

Note:
[1]FTC (freeze-thaw cycle): indicating the freeze-thaw stability of maltodextrin. FTC1, 3 and 5 respectively indicate the transparency of 30% maltodextrin after 1, 3, and 5 freeze-thaw cycles.

Transparency was represented by transmittance measured at 620 nm using a spectrophotometer.

What is claimed is:

1. A method for producing branched maltodextrin, the method comprises:
    preparing a slurry of a starch by heating the starch in the presence of α-amylase and stirring,
    liquifying the starch slurry by spray liquefaction to generate liquified starch,
    cooling the liquified starch to 50° C. or lower,
    adding *Rhodothermus obamensis*-derived starch branching enzyme to the liquified starch, wherein 200 to 500 Units enzyme is added per gram of the liquified starch by dry weight,
    incubating the branching enzyme with the liquified starch at pH 6.5 to 7.0, at a temperature of 65° C. to 70° C., for a period of 6 hours to 12 hours,
    filtering the branching enzyme-treated starch,
    decolorizing the filtered starch, carrying out ion-exchange on the decolored starch, and
    concentrating the ion-exchanged starch to obtain the branched maltodextrin.

2. The method of claim 1, wherein the step of adding *Rhodothermus obamensis*-derived starch branching enzyme to the liquified starch comprises:
    adding 500 Units starch branching enzyme per gram of the liquefied starch on a dry basis;
    adjusting the pH to 6.5, and
    incubating the starch branching enzyme with the liquified starch at 70° C. for 6 to 8 hours.

3. The method of claim 1, wherein the method further comprises a step of spray drying.

4. The method of claim 2, wherein the method further comprises a step of spray drying.

5. The method of claim 2,
    wherein the step of preparing a slurry of a starch by heating the starch in the presence of α-amylase and stirring, comprises:
    preparing starch milk from the starch,
    heating the starch milk,
    adding α-amylase and calcium chloride to the starch milk, and
    stirring the starch milk;
    wherein after the step of incubating the branching enzyme with the liquified starch, the starch branching enzyme is deactivated by heating;
    wherein the step of decolorizing comprises adding activated carbon; and
    wherein the step of carrying out ion-exchange, thereby, removes metal salt and pigment from the decolored starch.

6. The method of claim 5, wherein a dextrose equivalent (DE) value of the branched maltodextrin produced by the method is 2 to 20.

7. The method of claim 5, wherein the starch is selected from a group of consisting of: common maize starch, tapioca starch, potato starch, waxy maize starch, sweet potato starch, rice starch, and wheat starch;

wherein the concentration of the starch milk is 5% to 45% by weight;

wherein the starch milk is heated to 60° C. to 70° C.;

wherein the α-amylase is added in an amount of 10 to 15 Units per gram of the starch milk on a dry basis, and pH is then adjusted to 5.5 to 6.5 after the α-amylase is added; and wherein calcium chloride is added in an amount of 0.1% to 0.2% on a dry basis.

8. The method of claim 5, wherein the step of liquifying the starch slurry comprises two rounds of spray liquefaction.

9. The method of claim 5, wherein the two rounds of spray liquefaction comprises a first round of spraying and a second round of spraying, wherein the first round of spraying is performed at a material pressure of 0.35 MPa, a steam pressure of 0.1 MPa, and a temperature of 102° C. to 110° C. for 5 minutes to 15 minutes; and wherein the second round of spraying is performed at a material pressure of 0.35 MPa, a steam pressure of 0.3 MPa, and a temperature of 130° C. to 140° C., for 5 minutes.

10. The method of claim 5, wherein the step of incubating the branching enzyme with the liquified starch is performed at 65° C. to 70° C. for 6 hours.

11. The method of claim 2, (a) wherein the step of preparing a slurry of a starch by heating the starch in the presence of α-amylase and stirring, comprises:

preparing starch milk from the starch, heating the starch milk to 60° C. to 70° C., adding α-amylase to the starch milk in an amount of 10 to 15 Units per gram of the starch milk on a dry basis and calcium chloride in an amount of 0.1% to 0.2% on a dry basis, stirring, and adjusting the pH to 5.5 to 6.5, wherein the starch is selected from a group of consisting of: common maize starch, tapioca starch, potato starch, waxy maize starch, sweet potato starch, rice starch and wheat starch;

wherein the concentration of the starch milk is 5% to 45% by weight;

(b) wherein the step of liquifying the starch slurry by spray liquefaction to generate liquified starch is performed in two rounds of spray liquefaction, wherein the two rounds of spray liquefaction comprises a first round of spraying and a second round of spraying, wherein the first round of spraying is performed at a material pressure of 0.35 MPa, a steam pressure of 0.1 MPa, and a temperature of 102° C. to 110° C. for 5 minutes; and wherein the second round of spraying is performed at a material pressure of 0.35 MPa, a steam pressure of 0.3 MPa, and a temperature of 130° C. to 140° C. for 5 minutes.

12. A branched maltodextrin produced by the method of claim 2.

13. The method of claim 1, wherein transparency of the branched maltodextrin produced by the method is selected from one of 99.8%, 99.8% and 99.9% transmittance with DE values of 5, 10 and 15, respectively, when stored at 4° C. for 10 days, wherein the transparency is based on a 30% by weight aqueous solution of the branched maltodextrin.

14. The method of claim 13, wherein the transparency is one of 97.6% and 98.7% transmittance after 60 days of storage at 4° C. for branched maltodextrin having DE values of 10 and 15, respectively.

* * * * *